United States Patent
Meijide Garcia

(10) Patent No.: US 6,513,169 B1
(45) Date of Patent: Feb. 4, 2003

(54) BAND FOR CLOSING CORSETS

(75) Inventor: Jose Luis Meijide Garcia, Mostoles (ES)

(73) Assignee: Prim, S.A., Mostoles (ES)

( * ) Notice: Subject to any disclaimer, the term of this patent is extended or adjusted under 35 U.S.C. 154(b) by 0 days.

(21) Appl. No.: 09/719,356

(22) PCT Filed: Jun. 11, 1998

(86) PCT No.: PCT/ES98/00168

§ 371 (c)(1),
(2), (4) Date: Dec. 11, 2000

(87) PCT Pub. No.: WO99/63848

PCT Pub. Date: Dec. 16, 1999

(51) Int. Cl.[7] .................................................. A41F 9/00
(52) U.S. Cl. .......................................... 2/311; 450/141
(58) Field of Search ................................ 450/119, 122, 450/129, 134, 136, 139, 141; 2/311, 312, 91, 43, 44, 338, 336; 128/90.1, 96.1, 99.1, 100.1, 101.1

(56) References Cited

U.S. PATENT DOCUMENTS

| 1,665,502 A | 4/1928 | Kellogg |
| 1,736,128 A | 11/1929 | Pease |
| 2,017,679 A | 10/1935 | Allis |
| 2,066,536 A | 1/1937 | Mead |
| 2,406,528 A | 8/1946 | Blair |
| 3,091,774 A | 6/1963 | Shular |

*Primary Examiner*—Gloria Hale

(57) ABSTRACT

A band having an eyelet and a housing for stays for use in clothing and orthopedic items is disclosed that includes a double band having lateral seams, a tension resistant lace positioned on one side of the double band, the tension resistant lace connected at a spacing to the double band at points, and at least one half-wave shaped segment formed of the tension resistant lace between the points.

5 Claims, 1 Drawing Sheet

BAND FOR CLOSING CORSETS

OBJECT OF THE INVENTION

The present invention relates to a band with eyelets and a housing for stays, particularly supporting bands in closing means for corsets acting as stay protection sheaths in corsets and similar articles having a resurfacing of one of its sides and incorporating a number of lace segments including free areas that define eyelets along the band.

BACKGROUND OF THE INVENTION

Protection bands that act as stay sheaths are widely known and used in female clothing in general, and particularly in orthopedic corsets.

An example of the above-mentioned protection band is the sturdy woven band of Utility Model No. 013712, "Stay protector sheath in orthopedic corsets and the like" provided with a perimetral seam to prevent the stay ends from sliding out of the band.

However, the prior art clothing items edge eyelets are unnecessarily thick due to the conventional construction of the eyelet, which is riveted to and salient from the rest of the item, thus unnecessarily increasing the perimeter of the clothing item as it is rolled around the user's body, and therefore also increasing the latter's circumference.

Accordingly, there is a need for bands that eliminate the afore-mentioned shortcomings of the prior art.

DESCRIPTION OF THE INVENTION

The present invention relates to a band, preferably woven band, with eyelets and housings for stays. In particular, bands that house the stays and encase them are for the purposes of conventional uses, including for corsets and other similar elements in clothing items.

The invention is characterised by a particular construction of the band, which is provided in one of its sides, with a number of segments that are resurfaced. These segments house. a number of corresponding segments of laces of equal 10 lengths, in any construction of the latter, and have tension resistance properties suitable for their purpose.

The band is preferably formed by a double construction, as well as the sewn edges, so that the stay may be housed therein, and is reinforced on its sides with the consecutive seams of the lace segments.

The aforementioned lace defines, in its free areas segments that extend markedly outwards, forming half-wave crest projections.

These crest projections define eyelets that are displaced equidistant from each other along the band, the equidistance maintained by the corresponding segments that are joined to the band.

The eyelets are laterally and continuously positioned and are used to insert further 25 conventional laces for tightening and closing in corsets, using all or some of the eyelets as desired.

In any case the reinforcements on the sides of the band secure the eyelets along the band segment with which they are in contact, as opposed to the conventional construction in which each eyelet is in a weakened area of the support, decreasing risk of tearing.

In the construction of a corset, it is desirable to add to this arrangement of bands with eyelets and adjustments and closing laces portions of a complementary fabric to which they are sewn in order to obtain the aforementioned item.

DESCRIPTION OF THE DRAWINGS

Further characteristics of the present invention will become apparent in 5 view of the accompanying drawings where, for purposes of illustration only and in no way meant to define the limits of the invention, the following is shown.

PREFERRED EMBODIMENT OF THE INVENTION

Figure 1:
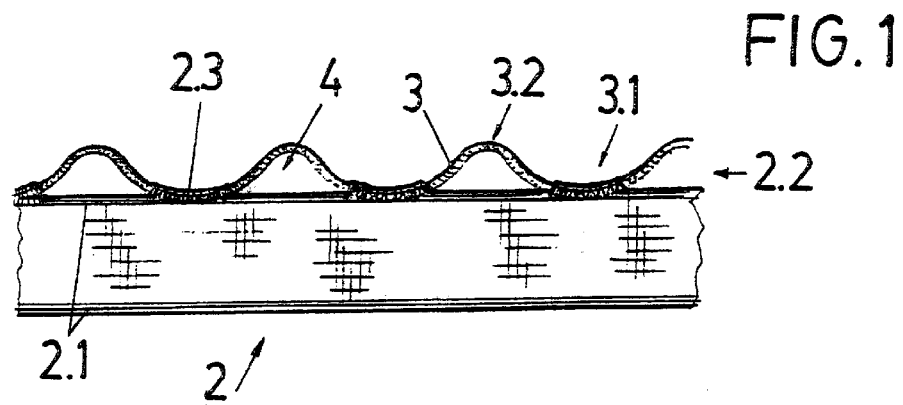
FIG. 1 shows the band of the invention in one of its segments, sectioned in order to show its construction more clearly.
Figure 2:
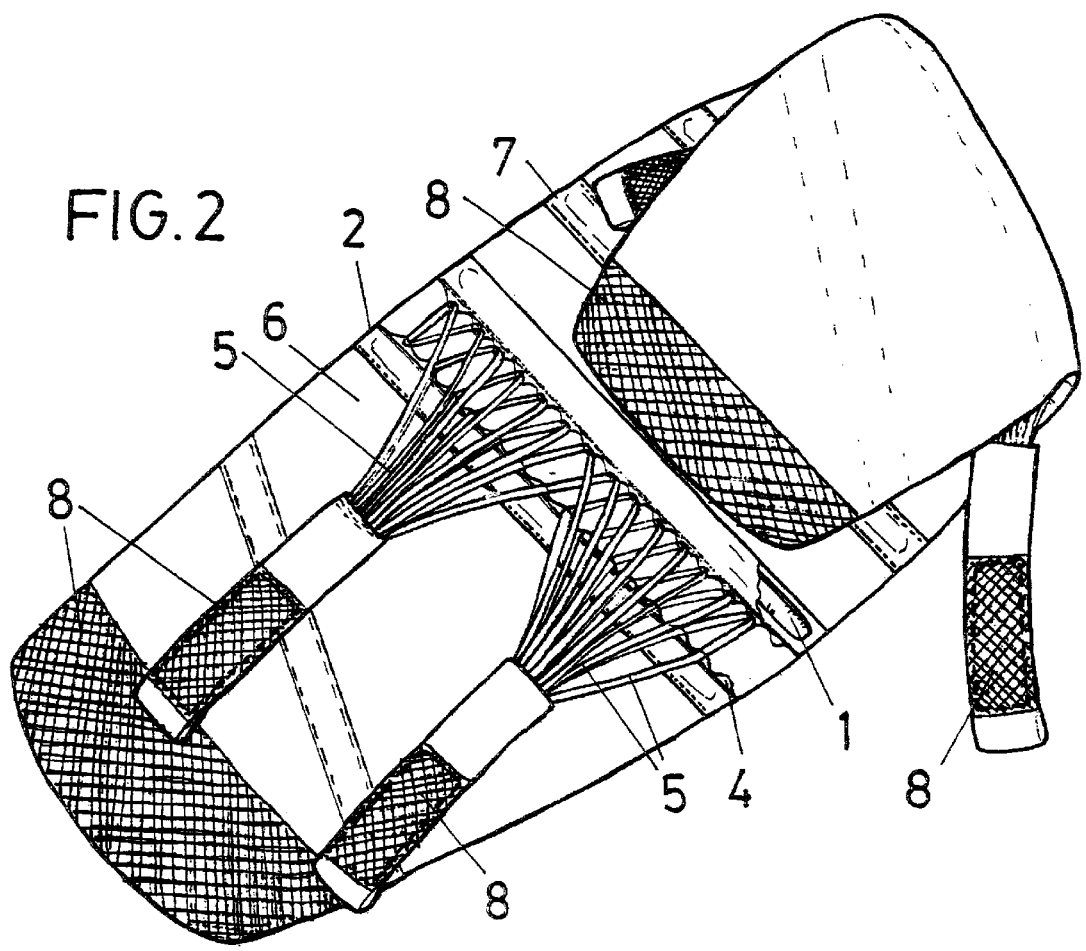
FIG. 2 shows the band of FIG. 1 incorporated in an example of an embodiment as a corset which is described below, open and ready to be used.

In view of the above, the present invention relates to a band with eyelets and housings or stays, whether the band is woven or not, to house stays (1) used in clothing or orthopedic items. The band is characterised by a double band (2) with lateral seams (2.1) and provided on one of its sides (2.2) with a lace (3) resistant to tension, connected at a spacing to band (2) at points (3.1) provided with suitable means, the spacing facilitating the formation of half wave segments (3.2) of lace (3) at junction points.

Half wave segments (3.2) of lace (3), can be set at spacings that are even or uneven separations, and are used as eyelets (4) for tightening and closing laces (4) of the item.

Included in a corset incorporating the bands (2) with eyelets (4) are fabric portions (6) sewn intermediately, and can incorporate further conventional bands (7) with more stays (1), as well as external segments provided with conventional closing means, such as self-adhering textile items (8).

This description is not continued in the understanding that any expert in the field would have sufficient information to comprehend the scope of the invention and the advantages derived thereof as well as to be capable of reproducing it.

It is also understood that as long as the essence of the invention remains unaltered any variations in materials, shape, size and arrangement of the elements may vary within the same characterization.

The terms employed in the description and its meaning must always be understood in a non-limiting manner.

What is claimed is:

1. A band having an eyelet and a housing for stays for use in clothing and orthopedic items, comprising:
   a double band having lateral seams;
   a tension resistant lace positioned on one side of said double band, said tension resistant lace connected at a spacing to said double band at points; and
   at least one half-wave shaped segment formed of said tension resistant lace between said points.

2. The band having an eyelet and a housing for stays according to claim 1 wherein said at least one half-wave shaped segment is used as an eyelet for tightening and closing said items.

3. The band having an eyelet and a housing for stays according to claim 1 wherein fabric portions are intermediately woven to said double band.

4. The band having an eyelet and a housing for stays according to claim 3 wherein said fabric portions incorporate additional bands having stays.

5. The band having an eyelet and a housing for stays according to claim 3 wherein said double bands include a self-adhering textile element.

* * * * *